United States Patent
Koo

(10) Patent No.: US 11,897,824 B2
(45) Date of Patent: Feb. 13, 2024

(54) METHOD OF PREPARING ACTIVATED MINERAL SOLUTION

(71) Applicant: Dong Chan Koo, Seongnam-si (KR)

(72) Inventor: Dong Chan Koo, Seongnam-si (KR)

( * ) Notice: Subject to any disclaimer, the term of this patent is extended or adjusted under 35 U.S.C. 154(b) by 644 days.

(21) Appl. No.: 17/155,214

(22) Filed: Jan. 22, 2021

(65) Prior Publication Data

US 2021/0237006 A1   Aug. 5, 2021

(30) Foreign Application Priority Data

Jan. 30, 2020  (KR) .................. 10-2020-0011143

(51) Int. Cl.
| | | |
|---|---|---|
| B01F 3/12 | (2006.01) | |
| B01F 1/00 | (2006.01) | |
| C05D 9/00 | (2006.01) | |
| C01F 11/06 | (2006.01) | |
| C25B 15/02 | (2021.01) | |
| C25B 1/18 | (2006.01) | |
| C25B 1/50 | (2021.01) | |
| C01F 11/16 | (2006.01) | |
| C12N 1/20 | (2006.01) | |
| C22B 3/18 | (2006.01) | |

(52) U.S. Cl.
CPC ................ *C05D 9/00* (2013.01); *C01F 11/06* (2013.01); *C01F 11/16* (2013.01); *C12N 1/20* (2013.01); *C22B 3/18* (2013.01); *C25B 1/18* (2013.01); *C25B 1/50* (2021.01); *C25B 15/02* (2013.01)

(58) Field of Classification Search
CPC ... C05D 9/00; C05D 9/02; C05G 1/00; C05G 3/00; C01F 11/06; C01F 11/16; C25B 15/02; C25B 1/18; C25B 1/50; C12N 1/20; C22B 3/18

See application file for complete search history.

(56) References Cited

U.S. PATENT DOCUMENTS 5,605,557 A * 2/1997 Hall .......................... C05C 5/04
                                                        71/62

FOREIGN PATENT DOCUMENTS

| CN | 106 748 330 A | * | 5/2017 | ............... C05D 1/00 |
|---|---|---|---|---|
| CN | 106 892 750 A | * | 6/2017 | ............... C05G 3/80 |
| CN | 110 194 682 A | * | 9/2019 | ............... C05D 9/00 |
| DE | 3 640 785 C | * | 4/1988 | ............... C05D 9/00 |
| JP | 06 141 671 A | * | 5/1994 | ............... C05D 9/00 |
| KR | 2000 0 001 061 A | * | 1/2000 | ............... C05D 9/00 |
| KR | 10-0738898 | | 7/2007 | |
| KR | 10-0938606 | | 1/2010 | |
| KR | 10-2010-0138160 | | 12/2010 | |
| KR | 10-1021303 | | 3/2011 | |

* cited by examiner

*Primary Examiner* — Timothy C Vanoy
(74) *Attorney, Agent, or Firm* — CANTOR COLBURN LLP

(57) ABSTRACT

Provided is a method of preparing an activated mineral solution, which includes steps of pulverizing granite and/or vermiculite into a powder by grinding, subjecting the powder to an electrolysis treatment, dissolving the powder in an aqueous ammonia solution and an acidic solution to prepare a mixed solution, emitting ultrasonic waves on the mixed solution, introducing microorganisms onto the mixed solution, and neutralizing the mixed solution, in which the mineral is selected from the group consisting of Fe, Mg, Al, Ti, K, Ca, Mn, Nb, P, Na, Zn, V, Cr, Ni, Si, B, Cu, Li, Ga, Co, Sr, In, Rb, Sb, Ta, Y, and combinations thereof.

10 Claims, 1 Drawing Sheet

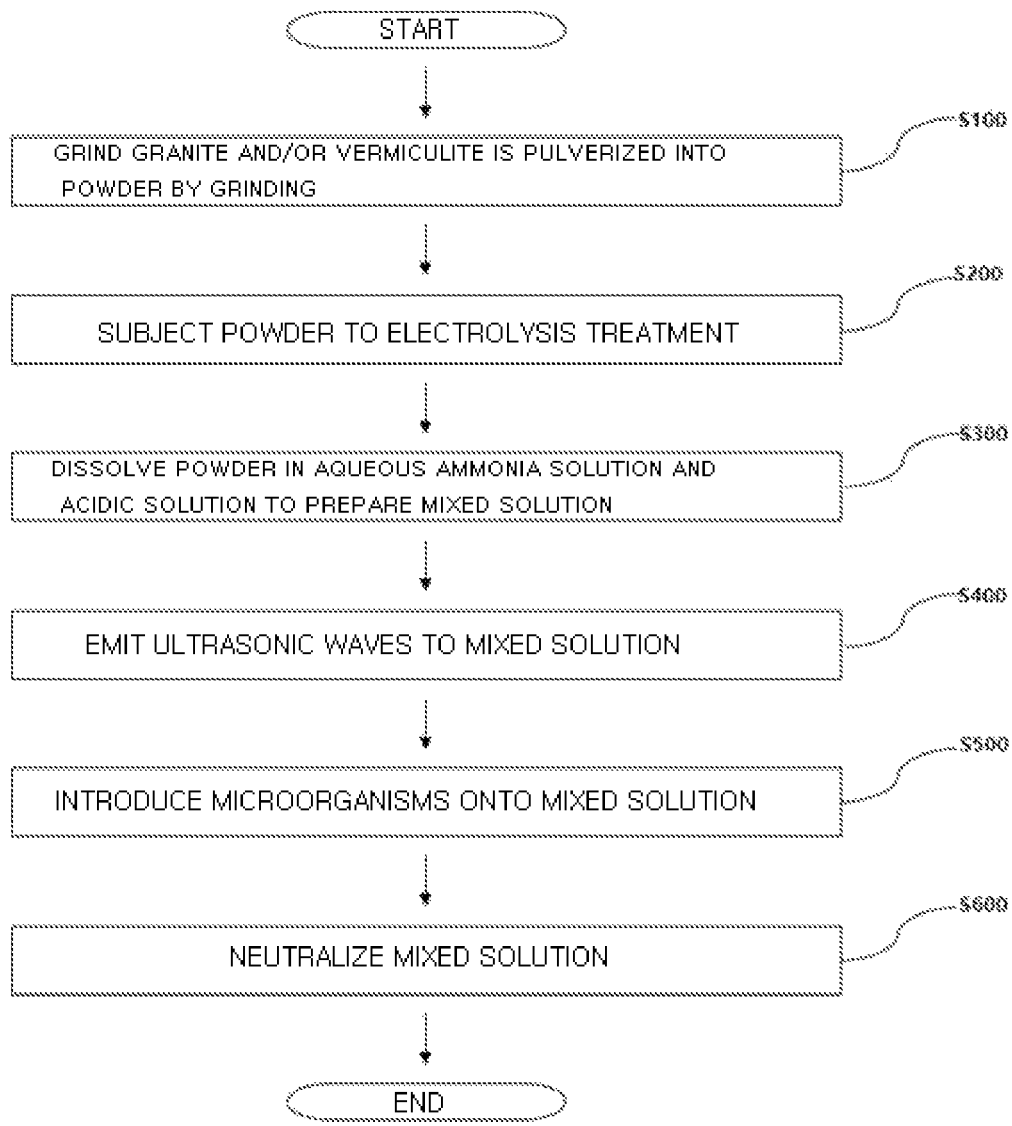

METHOD OF PREPARING ACTIVATED MINERAL SOLUTION

CROSS-REFERENCE TO RELATED APPLICATIONS

This patent application claims priority under 35 U.S.C. § 119 to Korean Patent Application No. 10-2020-0011143 filed on Jan. 30, 2020, the entire contents of which are incorporated by reference herein.

TECHNICAL FIELD

The present disclosure relates to a method of preparing an activated mineral solution.

BACKGROUND

Minerals in the soil can be lost into groundwater and rivers due to leaching and eluviation caused by meteorological phenomena such as snow and rain, and may also be depleted by continuous crop cultivation in limited places. The amount of minerals required by living organisms such as plants and animals is only a very small amount, but if any one component is out of balance or is deficient in a significant amount, it causes physiological disorders in living organisms, and these physiological disorders are not easily recovered and consequently inhibit plant growth, causing enormous economic losses. Animals may supplement minerals from plants or other animals, but since plants grow in a fixed place, the animals are vulnerable to mineral depletion due to continuous crop cultivation. In order to solve the above problems, minerals lost and depleted in the soil are artificially replenished, and these substances are referred to as fertilizers. Due to the recent development of chemical fertilizers, farmers generally use chemical fertilizers for crop cultivation such as paddy fields, fields or green houses. However, while these chemical fertilizers may provide the advantage of increased yield of agricultural crops, they also cause soil acidification and, when used for a long period of time, cause problems such as weakening fertility of soil.

The organic fertilizer fertilization is recommended to improve the problems of these chemical fertilizers, but because the organic fertilizers require the production process that is cumbersome and also require considerable labor for fertilization, general farmers often resort to using organic composts that are mainly commercialized and sold. The manufacturers of the organic compost mainly use sawdust to manufacture and sell unfermented compost, but the fact is that the farmers avoid use of the unfermented compost that is being manufactured and sold, for reasons such as foul smell generated due to gases such as ammonia generated after fertilization, hindered crop grow, and so on.

On the other hand, granite occupies a high proportion in domestic aggregate production mines, and can be used as a fertilizer for various elements such as Si, Fe, Mg, and Mn contained therein. However, when granite itself is used as a fertilizer, nutrients may not be easily supplied to the soil, such that research is being conducted to find a way to supply it in the form of a mineral solution. When nutrients are supplied in the form of a mineral solution, not only plants but also living organisms such as animals and humans can absorb minerals well, and thus be able to prevent physiological disorders caused by mineral deficiency.

Korean Registered Patent Publication No. 10-1021303, which is the background technology of the present disclosure, relates to a functional fertilizer composition containing a natural mineral component and a method for manufacturing the same. The above registered patent simply mixes and agitates vermiculite and sulfur to prepare a functional fertilizer composition, but does not recognize electrolysis treatment, ultrasonic irradiation, microbial injection processes, and the like.

SUMMARY

The present disclosure is made to solve the problems of the related art described above, and an object thereof is to provide a method of preparing an activated mineral solution.

However, the technical problem to be achieved by the embodiments of the present disclosure is not limited to the technical problem as described above, and other technical problems may exist.

As a technical means for achieving the technical problems described above, a method of preparing an activated mineral solution according to a first aspect of the present disclosure is provided, which includes steps of pulverizing granite and/or vermiculite into a powder by grinding, subjecting the powder to an electrolysis treatment, dissolving the powder in an aqueous ammonia solution and an acidic solution to prepare a mixed solution, emitting ultrasonic waves on the mixed solution, introducing microorganisms onto the mixed solution, and neutralizing the mixed solution, in which the mineral is selected from the group consisting of Fe, Mg, Al, Ti, K, Ca, Mn, Nb, P, Na, Zn, V, Cr, Ni, Si, B, Cu, Li, Ga, Co, Sr, In, Rb, Sb, Ta, Y, and combinations thereof.

According an exemplary embodiment, the step of preparing the mixed solution or the step of emitting the ultrasonic wave may be performed under an elevated temperature condition, but is not limited thereto.

According an exemplary embodiment, the elevated temperature condition may include increasing the temperature in a range of 5° C./h to 30° C./h, but is not limited thereto.

According an exemplary embodiment, the electrolysis treatment may be performed under a boosted voltage condition, but is not limited thereto.

According an exemplary embodiment, the boosted voltage condition may include increasing the applied voltage within a range of 0.1 V/min to 10 V/min, but is not limited thereto.

According an exemplary embodiment, the acidic solution may have a pH of 0.1 to 3, but is not limited thereto.

According to an exemplary embodiment, the microorganisms may include any microorganism selected from the group consisting of *Bacillus subtilis*, *Bacillus methylotrophicus*, *Bacillus vallismortis*, *Streptomyces* sp., *Trichoderma* sp., *Paenibacillus kribbensis*, *Pseudomonas fluorescens*, *Acinetobacter calcoaceticus*, *Auctusimonas hordei*, and combinations thereof, but is not limited thereto.

According an exemplary embodiment, before performing the step of introducing the microorganisms, a step of adjusting the pH of the mixed solution may be additionally included, but the present disclosure is not limited thereto.

According an exemplary embodiment, the frequency of the ultrasonic wave may be 0.1 MHz to 20 MHz, but is not limited thereto.

According an exemplary embodiment, the average particle size of the powder may be 0.1 μm to 1,000 μm, but is not limited thereto.

According an exemplary embodiment, the method of preparing a mineral solution may further include an ion exchange step, but is not limited thereto.

While certain means to solve the problems of the related art are described above, these are merely exemplary and should not be construed as limiting the present disclosure. In addition to the exemplary embodiments described above, additional embodiments may exist in the drawings and

DETAILED DESCRIPTION OF THE INVENTION

According to the above means for solving the problems of the related art, the method for preparing an activated mineral solution according to the present disclosure may extract various minerals from natural granite, vermiculite, and a mixture of granite and vermiculite. The extracted minerals can be used in various fields requiring minerals, such as sewage treatment processes, algae control, pharmaceuticals, and food industries, as well as agricultural fertilizers.

However, the effect obtainable in the present disclosure is not limited to those described above, and other effects may exist.

BRIEF DESCRIPTION OF THE DRAWING

The above and other objects, features and advantages of the present disclosure will become more apparent to those of ordinary skill in the art by describing in detail exemplary embodiments thereof with reference to the accompanying drawing, in which:

FIG. 1 is a flow chart showing a method of preparing a mineral solution according to an embodiment of the present disclosure.

DETAILED DESCRIPTION OF THE DISCLOSURE

Hereinafter, preferred embodiments of the present disclosure will be described in detail with reference to the accompanying drawings so that those with ordinary knowledge in the art can easily achieve the present disclosure.

However, the description proposed herein is just a preferable embodiment for the purpose of illustrations only, not intended to limit the scope of the disclosure, so it should be understood that other equivalents and modifications could be made thereto without departing from the scope of the disclosure. The functions or elements in the drawings that are irrelevant to the present disclosure will not be described for the sake of clarity, and throughout the description, the like reference numerals are used to denote the same or similar elements.

Throughout the description, when a portion is stated as being "connected" to another portion, it encompasses not only when the portions are "directly connected", but also when the portions are "electrically connected" while being intervened by another element present therebetween.

Throughout the description, when one member is positioned "on", "above", "on an upper end of", "under", "beneath", and "on a lower end of" the other member, this includes not only the case where the one member is positioned in contact with the other member, but also the case where another member is present between the one and the other members.

Throughout the description, when a portion is stated as "comprising (including)" an element, unless specified to the contrary, it intends to mean that the portion may additionally include another element, rather than excluding the same.

The term "about or approximately" or "substantially" is intended to have meanings close to numerical values or ranges specified with an allowable error and intended to prevent accurate or absolute numerical values disclosed for understanding of the present disclosure from being illegally or unfairly used by any unconscionable third party. In addition, throughout the description, the term "step of ~" or "~ step" does not mean "step for ~".

Throughout the description, the term "combination thereof" included in Markush type description means mixture or combination of one or more components, steps, operations and/or elements selected from a group consisting of components, steps, operation and/or elements described in Markush type and thereby means that the disclosure includes one or more components, steps, operations and/or elements selected from the Markush group.

Throughout the description, the phrase "A and/or B" means "A or B", or "A and B".

Hereinafter, the present disclosure will be explained in detail with reference to embodiments, examples, and drawings. However, the present disclosure is not limited to the following embodiments, examples, and drawings.

As a technical means for achieving the technical problems described above, a method of preparing an activated mineral solution according to a first aspect of the present disclosure is provided, which includes steps of pulverizing granite and/or vermiculite into a powder by grinding, subjecting the powder to an electrolysis treatment, dissolving the powder in an aqueous ammonia solution and an acidic solution to prepare a mixed solution, emitting ultrasonic waves on the mixed solution, introducing microorganisms onto the mixed solution, and neutralizing the mixed solution, in which the mineral is selected from the group consisting of Fe, Mg, Al, Ti, K, Ca, Mn, Nb, P, Na, Zn, V, Cr, Ni, Si, B, Cu, Li, Ga, Co, Sr, In, Rb, Sb, Ta, Y, and combinations thereof.

The granite according to the present disclosure is a kind of felsic pluton, and refers to a rock including orthoclase, plagioclase, quartz, biotite, amphibole, muscovite, magnetite, garnet, zircon, apatite, pyroxene, and the like. In general, the granite refers to a material containing $SiO_2$ 49.4%, $Al_2O_3$ 9.46%, $K_2O$ 2.05%, $Na_2O$ 1.92%, CaO 10.4%, FeO 1.68%, $Fe_2O_3$ 8.09%, MgO 12.5%, $TiO_2$ 1.30%, $P_2O_5$ 0.40%, $MnO_2$ 0.17%, $Li_2O$ 0.01%, CuO 0.03%, $ZrO_2$ 0.01%, $V_2O_5$ 0.01%, $La_2O_3$ 0.01%, NiO 0.09%, $ZnO_2$ 0.02%, $Co_2O_3$ 0.01%, SrO 0.04%, $Nd_2O_5$ 0.03%, and other oxides.

The vermiculite according to the present disclosure means a mineral obtained by heating and expanding mica-based ore at a high temperature of 1,000° C. or higher. Since the mica-based ore contains moisture inside, the moisture expands when heated, and the volume may expand 5 to 10 times. The vermiculite may change color according to the content of iron oxide therein.

First, the granite and/or vermiculite is pulverized into powder by grinding (S100).

Preferably, granite, vermiculite, or a mixture of granite and vermiculite may be pulverized to prepare the mineral solution, but is not limited thereto.

According an exemplary embodiment, the average particle size of the powder may be 0.1 μm to 1,000 μm, but is not limited thereto. For example, the average particle size of the powder is about 0.1 μm to about 1,000 μm, about 1 μm to about 1,000 μm, about 10 μm to about 1,000 μm, about 50 μm to about 1,000 μm, about 100 μm to about 1,000 μm, About 125 μm to about 1,000 μm, about 150 μm to about 1,000 μm, about 175 μm to about 1,000 μm, about 200 μm to about 1,000 μm, about 250 μm to about 1,000 μm, about 300 μm to about 1,000 μm, about 400 μm to about 1,000 μm, about 500 μm to about 1,000 μm, about 600 μm to about 1,000 μm, about 700 μm to about 1,000 μm, about 800 μm to about 1,000 μm, about 900 μm to about 1,000 μm, about 0.1 μm to About 1 μm, about 0.1 μm to about 10 μm, about 0.1 μm to about 50 μm, about 0.1 μm to about 100 μm, about 0.1 μm to about 125 μm, about 0.1 μm to about 150 μm, about 0.1 μm to about 175 μm, about 0.1 μm to about 200 μm, about 0.1 μm to about 250 μm, about 0.1 μm to about 300 μm, about 0.1 μm to about 400 μm, about 0.1 μm to about 500 μm, about 0.1 μm to about 600 μm, About 0.1 μm to about 700 μm, about 0.1 μm to about 800 μm, about 0.1 μm to about 900 μm, about 1 μm to about 900 μm, about 10 μm to about 800 μm, about 50 μm to about 700 μm, about 100 μm to about 600 μm, about 125 μm to about 500 μm, about 150 μm to about 400 μm, about 175 μm to about 300 μm, or about 200 μm to about 250 μm, but is not limited thereto. Preferably, the average particle size of the powder may be about 150 μm to about 175 μm, but is not limited thereto. In this regard, as the size of the powder particles decreases, minerals of the granite and/or vermiculite may be easily leached into the solution.

According an exemplary embodiment, the pulverizing step may be performed by dry milling or wet milling, but is not limited thereto.

The dry milling according to the present disclosure means grinding an object in the air, and the wet milling means grinding an object in water or an organic solvent. In this regard, when the granite and/or vermiculite is wet milled, internal minerals may be leached into the water or the organic solvent, but the size of the powder particles may be reduced. In addition, when the granite and/or vermiculite is dry milled, the size of the powder particles may be larger than that of wet milling, and there is an advantage that there is no concern of the minerals of the granite and/or vermiculite being lost, although dust may be mixed into the powder.

Preferably, the pulverizing step may be performed by a dry milling process.

According an exemplary embodiment, the pulverizing step may further include a process of refining the powder, but is not limited thereto.

In the pulverizing step, dust may be mixed in the powder, and the dust may act as an impurity of the mineral solution, and thus, a refining process may be required.

When the powder is prepared by wet milling, the process of refining the powder may include steps of evaporating the water or the organic solvent containing the powder, centrifuging the powder, or filtering the water or organic solvent containing the powder, but is not limited thereto.

When the powder is prepared by dry milling, the process of refining the powder may include steps of filtering the powder, centrifuging the powder, or separating using a difference in density of the powder, but is not limited thereto.

Next, the powder is subjected to electrolysis treatment (S200).

When a voltage is applied to the powder for the electrolysis treatment, the bonds among the ionic materials in the powder may be broken and the bonding force may be weakened, so that more minerals may be leached during the preparation of a mineral solution to be described below.

According an exemplary embodiment, the electrolysis treatment step may be performed under a boosted voltage condition, but is not limited thereto. In this regard, the boosted voltage condition means that the applied voltage is increased at a constant rate for a predetermined time.

According an exemplary embodiment, the boosted voltage condition may include increasing the applied voltage within a range of 0.1 V/min to 10 V/min, but is not limited thereto. For example, the boosted voltage condition may include increasing the applied voltage within a range of about 0.1 V/min to about 10 V/min, about 1 V/min to about 10 V/min, about 2 V/min to about 10 V/min, about 3 V/min To about 10 V/min, about 4 V/min to about 10 V/min, about 5 V/min to about 10 V/min, about 6 V/min to about 10 V/min, about 7 V/min to about 10 V/min, about 8 V/min to about 10 V/min, about 9 V/min to about 10 V/min, about 0.1 V/min to about 1 V/min, about 0.1 V/min to about 2 V/min, about 0.1 V/min to about 3 V/min, about 0.1 V/min to about 4 V/min, about 0.1 V/min to about 5 V/min, about 0.1 V/min to about 6 V/min, about 0.1 V/min to about 7 V/min, about 0.1 V/min to about 8 V/min, about 0.1 V/min to about 9 V/min, about 1 V/min to about 9 V/min, about 2 V/min to about 8 V/min, about 3 V/min to about 7 V/min, about 4 V/min to about 6 V/min, or about 5 V/min, but is not limited thereto.

According an exemplary embodiment, when the voltage is increased according to the boosted voltage condition, the final voltage may be 6 V to 6,000 V, but is not limited thereto.

According to an exemplary embodiment, the powder electrolysis treatment step is performed under a condition of increasing the applied voltage according to the boosted voltage condition, or under a condition in which the voltage applied to the powder is maintained within 6 V to 6,000 V, but is not limited thereto. In this regard, a condition in which the voltage applied to the powder is maintained at a constant value may be referred to as a constant voltage condition.

The voltage may be evenly applied to the entire powder when the electrolysis treatment is performed under the boosted voltage condition. However, when the electrolysis treatment is performed under the constant voltage condition, the voltage application is focused at a region of the powder that is close to the electrode, while the voltage is not applied to a region of the powder that is farther away from the electrode, so that ionic bond may not be broken. Therefore, the electrolysis treatment step may further include agitating while applying a voltage.

Next, the powder is dissolved in an aqueous ammonia solution and an acidic solution to prepare a mixed solution (S300).

According an exemplary embodiment, the mixed solution may include a polar solvent such as water, alcohol, ether, and so on, but is not limited thereto.

Along with the molecules or ions that can accept electron pairs, the aqueous ammonia solution according to the present disclosure includes ligand such as $NH_3$, $NH_4OH$, $NH_4^+$, and $OH^-$, and so on that have the ability to form coordinate covalent bonds and the ability to form ion-dipole bonds such that the aqueous ammonia solution can react with the powder to form a complex compound. Specifically, the ligand of the aqueous ammonia solution reacts with inorganic metal ions in the powder to form complex ions, thereby refining the powder.

According an exemplary embodiment, the acidic solution may have a pH of 0.1 to 3, but is not limited thereto.

The acidic solution dissolves the powder so as to leach out the inorganic material contained therein. In this regard, the acidic solution may contain strong acid such as hydrochloric acid, sulfuric acid, nitric acid, and so on.

In this regard, when the granite and/or vermiculite is ground to prepare an untreated powder and then dissolved with sulfuric acid without a separate process, 2% to 3% of the minerals of the untreated powder may be leached into the sulfuric acid.

However, the method of preparing a mineral solution according to the present disclosure may further include the steps of subjecting the powder to an electrolysis treatment, dissolving the powder in an aqueous ammonia solution and an acidic solution, introducing microorganisms into the mixed solution to be described below, and emitting ultrasonic waves on the mixed solution, thereby obtaining 10% to 20% of the mineral of the powder.

According an exemplary embodiment, the step of preparing the mixed solution or the step of emitting ultrasonic waves to be described below may be performed under an elevated temperature condition, but is not limited thereto. In this regard, the elevated temperature condition means that the temperature of the powder is increased at a predetermined rate for a predetermined time.

According an exemplary embodiment, the elevated temperature condition may include increasing the temperature in a range of 5° C./h to 30° C./h, but is not limited thereto. For example, the rate of temperature elevation under the elevated temperature condition is about 5° C./h to about 30° C./h, about 10° C./h to about 30° C./h, about 15° C./h to about 30° C./h, about 20° C./h to about 30° C./h, about 25° C./h to about 30° C./h, about 5° C./h to about 25° C./h, about 5° C./h to about 20° C./h, about 5° C./h to about 15° C./h, about 5° C./h to about 10° C./h, about 10° C./h to about 25° C./h, or about 15° C./h to about 20° C./h, but is not limited thereto.

According an exemplary embodiment, the step of preparing the mixed solution or the step of emitting ultrasonic waves to be described below may be performed at a temperature of 40° C. to 150° C., but is not limited thereto. In this regard, a condition in which the temperature of the mixed solution is maintained at a constant value may be referred to as a constant temperature condition.

The temperature conditions of the step of preparing the mixed solution and the step of emitting the ultrasonic wave may be the same or different. For example, when the step of preparing the mixed solution is performed under a first elevated temperature condition, the step of emitting the ultrasonic wave may be performed under a second elevated temperature condition or a first temperature condition. In addition, when the step of preparing the mixed solution is performed at a second temperature, the step of emitting the ultrasonic wave may be performed under a third elevated temperature condition or a third temperature condition. In this regard, the first to third elevated temperature conditions mean the rates of temperature elevation that satisfy the elevated temperature condition, and the first to third temperatures may mean the temperatures that satisfy the temperature condition of 40° C. to 200° C.

The first to third elevated temperature conditions, or the first to third temperatures may be the same or different.

Specifically, when the step of preparing the mixed solution and the step of emitting the ultrasonic wave are performed under the elevated temperature conditions, the temperature of the entire powder may increase, which may in turn increase the quality of the mineral solution. In addition, when the step of preparing the mixed solution or the step of emitting ultrasonic waves to be described below is performed under the constant temperature condition, the influence of the temperature is less in the region of the powder that is farther away from where the temperature is applied.

Next, the ultrasonic waves are emitted to the mixed solution (S400).

According an exemplary embodiment, the frequency of the ultrasonic wave may be 0.1 MHz to 20 MHz, but is not limited thereto.

When the ultrasonic waves are emitted to the mixed solution, the chain structure in the water molecule may be cut to generate OH− and H+ ions. The OH− and H+ may react with the powder, that is, react with the substances in the granite and/or vermiculite to form a hydrous coordination compound.

Next, microorganisms are introduced onto the mixed solution (S500).

According to an exemplary embodiment, the microorganisms may include any microorganism selected from the group consisting of *Bacillus subtilis*, *Bacillus methylotrophicus*, *Bacillus vallismortis*, *Streptomyces* sp., *Trichoderma* sp., *Paenibacillus kribbensis*, *Pseudomonas fluorescens*, *Acinetobacter calcoaceticus*, *Auctusimonas hordei*, and combinations thereof, but is not limited thereto. For example, the microorganisms may be microorganisms of the genus *Bacillus*.

According an exemplary embodiment, before performing the step of introducing the microorganisms, a step of adjusting the pH of the mixed solution may be additionally included, but the present disclosure is not limited thereto.

According an exemplary embodiment, before performing the step of introducing the microorganisms, the step of adjusting the temperature of the mixed solution may be additionally included, but is not limited thereto.

In general, since the pH and temperature conditions that exhibit optimal activity are different depending on the type of microorganisms, it is necessary to adjust the pH and temperature of the mixed solution in order to activate the microorganisms.

In order to remove foul odors and harmful gases that may occur in an environment in which the mineral solution is used, the mineral solution may contain microorganisms. The related mineral solution contains a chemical deodorant, but the mineral solution according to the present disclosure can solve the problem of the chemical deodorant of the related art by including microorganisms, and since the use of some minerals of the mineral solution can breed the microorganisms, the shelf life problem can also be solved.

Next, the mixed solution is neutralized (S600).

In this regard, the neutralization according to the present disclosure means that the number of pH of the mixed solution is increased, and the neutralized mixed solution may have weak acidity, neutrality, or basicity.

According an exemplary embodiment, the processes performed in the mixed solution, that is, the step of emitting the ultrasonic wave, the step of introducing the microorganisms, and the step of neutralizing may not be determined in certain order, but are not limited thereto. For example, the processes performed in the mixed solution may be performed in the order of the steps of emitting the ultrasonic wave, introducing the microorganisms, and neutralizing, the steps of emitting the ultrasonic wave, neutralizing, and introducing the microorganisms, the steps of introducing the microorganisms, emitting the ultrasonic wave, and neutralizing, the steps of introducing the microorganisms, neutralizing, and emitting the ultrasonic wave, the steps of neutralizing, emitting the ultrasonic wave, and introducing the microorganisms, or, the steps of neutralizing, introducing the microorganisms, and emitting the ultrasonic wave, but is not limited thereto.

According an exemplary embodiment, the method of preparing a mineral solution may further include an ion exchange step, but is not limited thereto.

The mineral solution is prepared by processing the granite and/or vermiculite. In this regard, the content of minerals in the mineral solution may vary depending on the use, and some minerals may be present at an excess or small quantity depending on the content of the material itself. In order to overcome this problem, the method of preparing a mineral solution according to the present disclosure may balance the minerals by performing an ion exchange process.

According an exemplary embodiment, the mineral solution may be prepared into a power type compost through a drying process, but is not limited thereto.

According an exemplary embodiment, the mineral content in the mineral solution may be analyzed by atomic absorption spectroscopy or plasma emission spectroscopy, but is not limited thereto.

The present disclosure will be described in more detail through the following examples, although the following examples are for illustrative purposes only and are not intended to limit the scope of the present disclosure.

EXAMPLE 100 kg of powder having an average particle size of 160 μm was prepared by dry milling the granite lumps collected from Gwangcheon, Chungcheongnam-do, Korea and vermiculite collected from Godeok, Chungcheongnam-do, Korea. Next, a solution in which the powder was mixed with water was formed, and voltage was applied to the solution to electrolyze the powder. In this regard, the voltage was applied for 6 hours under the boosted voltage condition of 1 V/min.

Next, water was evaporated from the solution, and then the electrolyzed powder was mixed with 20 w/v % aqueous ammonia solution and 15 w/v % sulfuric acid to adjust the pH of the mixed solution to 2. Next, while emitting ultrasonic wave of 3 MHz to the mixed solution, the pH was adjusted so that the microorganisms of the *Bacillus* genus could survive, and then the *Bacillus* microorganisms were added. In this regard, the process of preparing the mixed solution and the process of emitting ultrasonic waves were performed for 3 hours at elevated temperature conditions of 10° C./h and 20° C./h, respectively.

Next, a mineral solution was prepared by neutralizing the pH of the mixed solution to 6.4 to 8.1.

In this regard, the step of ion-exchanging the mineral solution may be further included according to the use.

Comparative Example 1

A mineral solution was prepared in the same manner as in the above example, except that the electrolysis treatment was omitted.

Comparative Example 2

A mineral solution was prepared in the same manner as in the above example, except that the process of emitting ultrasonic wave was omitted.

Comparative Example 3

A mineral solution was prepared in the same manner as in the above example, except that the electrolysis treatment was performed under a predetermined voltage condition of 360 V for 1 hour.

Comparative Example 4

A mineral solution was prepared in the same manner as in the above example, except that the ultrasonic wave was emitted for 1 hour under a predetermined temperature condition of 60° C.

Experimental Example 1

The mineral content of the mineral solution according to the present disclosure was confirmed. The unit of the component is ppm, and the component content table is shown in Tables 1 and 2 below.

TABLE 1

| Component | Content of Example | Content of Comp. Ex. 1 | Content of Comp. Ex. 2 |
|---|---|---|---|
| Mg | 14,843 | 1,873 | 2,718 |
| Fe | 12,789 | 2,431 | 1,713 |
| Al | 7,891 | 727 | 538 |
| K | 3,657 | 1,357 | 728 |
| P | 571 | 259 | 419 |
| Ca | 397 | 342 | 319 |
| Ni | 149 | 130 | 117 |
| Mn | 81 | 67 | 65 |
| Cu | 67 | 51 | 32 |
| Na | 79 | 57 | 34 |

TABLE 2

| Component | Content of Example | Content of Comp. Ex. 3 | Content of Comp. Ex. 4 |
|---|---|---|---|
| Mg | 14,843 | 8,414 | 7,187 |
| Fe | 12,789 | 6,781 | 5,279 |
| Al | 7,891 | 3,246 | 3,541 |
| K | 3,657 | 2,179 | 1,877 |
| P | 571 | 413 | 527 |
| Ca | 397 | 308 | 209 |
| Ni | 149 | 79 | 57 |
| Mn | 81 | 61 | 23 |
| Cu | 67 | 41 | 38 |
| Na | 79 | 63 | 64 |

Referring to Tables 1 and 2, it can be seen that inorganic substances may be further leached out from the granite and/or vermiculite by the electrolysis treatment and the ultrasonic treatment. In addition, when the mineral solution is prepared while gradually increasing the temperature or voltage, it can be seen that more inorganic substances can be leached than when the mineral solution is prepared at a constant temperature.

In this regard, inorganic metals other than those mentioned in Tables 1 and 2 can be present in the mineral solution, but they omitted because they are trace amounts.

The foregoing description of the present disclosure is for illustrative purposes only, and those of ordinary skill in the art to which the present disclosure pertains will be able to understand that other specific forms can be easily modified without changing the technical spirit or essential features of the present disclosure. Therefore, it should be understood that the embodiments described above are illustrative and non-limiting in all respects. For example, each component described as a single type may be implemented in a distributed manner, and similarly, components described as being distributed may also be implemented in a combined form.

While the scope of the present disclosure is represented by the claims accompanying below, the meaning and the scope of the claims, and all the modifications or modified forms that can be derived from the equivalent concepts will have to be interpreted as falling into the scope of the present disclosure.

What is claimed is:

1. A method of preparing an activated mineral solution, comprising steps of:

pulverizing granite and/or vermiculite into a powder by grinding;
subjecting the powder to an electrolysis treatment;
dissolving the powder in an aqueous ammonia solution and an acidic solution to prepare a mixed solution;
emitting ultrasonic wave to the mixed solution;
introducing microorganisms onto the mixed solution; and
neutralizing the mixed solution to prepare a mineral solution,
wherein the step of electrolysis treatment is performed under a boosted voltage condition, and
the mineral is selected from the group consisting of Fe, Mg, Al, Ti, K, Ca, Mn, Nb, P, Na, Zn, V, Cr, Ni, Si, B, Cu, Li, Ga, Co, Sr, In, Rb, Sb, Ta, Y, and combinations thereof.

2. The method of claim 1, wherein the step of preparing the mixed solution, or the step of emitting the ultrasonic wave is performed under an elevated temperature condition.

3. The method of claim 2, wherein the elevated temperature condition includes increasing a temperature within a range of 5° C./h to 30° C./h.

4. The method of claim 1, wherein the boosted voltage condition includes increasing an applied voltage within a range of 0.1 V/min to 10 V/min.

5. The method of claim 1, wherein the acidic solution has a pH of 0.1 to 3.

6. The method of claim 1, wherein the microorganisms include any microorganism selected from the group consisting of *Bacillus subtilis, Bacillus methylotrophicus, Bacillus vallismortis, Streptomyces* sp., *Trichoderma* sp., *Paenibacillus kribbensis, Pseudomonas fluorescens, Acinetobacter calcoaceticus, Auctusimonas hordei*, and combinations thereof.

7. The method of claim 1, wherein, before performing the step of introducing the microorganisms, the method of preparing an activated mineral solution further comprises a step of adjusting a pH of the mixed solution.

8. The method of claim 1, wherein a frequency of the ultrasonic wave is 0.1 MHz to 20 MHz.

9. The method of claim 1, wherein an average particle size of the powder is 0.1 μm to 1,000 μm.

10. The method of claim 1, wherein the method of preparing an activated mineral solution further comprises a step of ion-exchanging.

* * * * *